United States Patent [19]

Outerbridge

[11] Patent Number: 4,852,558

[45] Date of Patent: Aug. 1, 1989

[54] COMPRESSIBLE BONE STAPLE

[76] Inventor: Howard K. G. Outerbridge, #502 - 713 Columbia Street, New Westminster, British Columbia, Canada, V3M 1B2

[21] Appl. No.: 79,266

[22] Filed: Jul. 29, 1987

[51] Int. Cl.⁴ .............................................. A61F 5/04
[52] U.S. Cl. ......................... 128/92 YF; 128/92 YC
[58] Field of Search ........... 128/82 YF, 92 YC, 92 Y; 411/457, 464, 465, 469, 479, 481, 508–510, 923

[56] References Cited

U.S. PATENT DOCUMENTS

| | | | |
|---|---|---|---|
| 3,385,299 | 5/1968 | Le Roy | 128/346 |
| 3,510,923 | 5/1970 | Blake | 128/346 |
| 3,601,127 | 8/1971 | Finegold | 128/346 |
| 3,604,414 | 9/1971 | Borges | 128/92 YL |
| 3,807,394 | 4/1974 | Attenborough | 128/92 YC |
| 3,862,631 | 1/1975 | Austin | 128/92 Y |
| 3,939,828 | 2/1976 | Mohr et al. | 128/92 YC |
| 3,960,147 | 6/1976 | Murray | 128/92 YC |
| 4,157,715 | 6/1979 | Westerhoff | 128/92 YZ X |
| 4,246,660 | 1/1981 | Wevers | 128/92 YC |
| 4,454,875 | 6/1984 | Pratt et al. | 128/92 YC |
| 4,570,623 | 2/1986 | Ellison et al. | 128/92 YC |
| 4,570,624 | 2/1986 | Wu | 128/92 VD |

FOREIGN PATENT DOCUMENTS

| | | | |
|---|---|---|---|
| 1239266 | 7/1960 | France | 128/92 YL |
| 1114407 | 9/1984 | U.S.S.R. | 128/92 YC |

Primary Examiner—Robert A. Hafer
Assistant Examiner—Kevin G. Rooney
Attorney, Agent, or Firm—Poms, Smith, Lande & Rose

[57] ABSTRACT

A bone staple comprising first and second staple legs and a slidably adjustable ratchet mechanism for coupling the legs together and for lockably positioning them a selected distance apart; thereby facilitating the application of compressive forces between the ends of a bone joined together with the staple.

11 Claims, 7 Drawing Sheets

COMPRESSIBLE BONE STAPLE

FIELD OF THE INVENTION

This application pertains to bone grasping and fastening systems such as bone staples for use in surgical orthopaedic procedures. More particularly, the application pertains to a compressible bone staple having a ratchet mechanism which facilitates lockable positioning of the staple legs at a selected distance apart from one another, thereby enabling the application of compressive forces to bones joined together with the staple.

BACKGROUND OF THE INVENTION

The prior art has evolved a variety of bone staples for use in surgical osteotomy procedures. Such staples conventionally have a pair of staple legs which are driven into the opposing ends of the bone segments which are to be joined together, and a mechanism for forcing the staple legs towards one another, thereby in turn forcing the ends of the bones together. U.S. Pat. No. 3,862,631 issued Jan. 28, 1975 for an invention of Roger Tilston Austin entitled "Surgical Implants" is typical of the prior art. Austin's "implant" takes the form of a staple with first and second legs. The first leg has a threaded projection which may be screwed into a threaded barrel provided on the second staple leg. The threaded projection on the first staple leg is made sufficiently long that it protrudes through the threaded barrel on the second staple leg, thereby facilitating the threaded fastening of a spring washer and a pair of lock nuts on the protruding end of the threaded projection. Once the staple has been driven into the bone, the lock nuts are tightened to draw the staple legs and thus the bone segments together. There are however a number of shortcomings to this arrangement. For example, bone staples are preferably made as small as reasonably practical to avoid undue patient discomfort caused by protrusion of staple components beneath the skin. Accordingly, the lock nuts of the Austin staple are comparatively small; however this makes it difficult to tighten the lock nuts at the surgical site, thus potentially enabling slippage of the bone segments relative to one another, or dislodgement of the staple. Moreover, it is difficult to apply adequate compressive forces between the ends of the bone without stripping the lock nuts. Austin's bone staple also has a relatively high profile. That is, the lock nuts, spring washers, threaded barrel and threaded projection of the staple must all be left protruding above the bone after the staple has been inserted. This can cause considerable patient discomfort and pain.

The present invention overcomes the foregoing disadvantages by providing a bone staple which can be easily manipulated by the surgeon to apply considerable compressive forces between the ends of bone segments joined together with the staple; which is not prone to slippage or dislodgement after placement; and which has a low profile, thus minimizing patient discomfort.

SUMMARY OF THE INVENTION

The invention provides a bone staple comprising first and second staple legs and a slidably adjustable ratchet means for coupling the legs together and for lockably positioning them a selected distance apart from one another. In one embodiment, the ratchet means comprises a first toothed member affixed to the first leg to project at an angle therefrom; a guide member affixed to the second leg to project at an angle therefrom, the guide member for coupling with the first toothed member, thereby positioning the first leg relative to the second leg; and, a second toothed member coupled to the guide member for ratchetably engaging the first toothed member.

In a basic tarsal osteotomy staple the first toothed member projects from the first leg at an angle of about 90° and the guide member projects from the second leg at an angle of about 90°.

In any embodiment of the invention the first toothed member preferably ratchetably engages the second toothed member inside the region between the first and second members.

A shield means may be provided on the guide member for preventing fouling of the region in which the first toothed member ratchetably engages the second toothed member.

Gripping means may be provided on the first and second legs respectively for gripping of the staple by a staple manipulating tool.

A reinforcing means may be affixed between the first leg and the first toothed member in order to hold the first leg in position relative to the first toothed member when force is applied to the bone staple. Similarly, a reinforcing means may be affixed between the second leg and the guide member for holding the second leg in position relative to the guide member when force is applied to the bone staple.

The staple legs may each be provided with retention means such as barbs for retaining the legs within bone into which the staple is driven.

The staple legs may be of different lengths and they may be of different cross-sections. For example, a metatarsal osteotomy staple would preferably have rounded legs of different lengths.

In a metatarsal osteotomy staple a hooked projection may be provided on the end of either or both staple legs.

In a high tibial osteotomy staple first toothed member may be stepped. An aperture may be provided in the stepped member for passage of a wire therethrough. The ends of the wire may be fastened over the second staple leg to hold the staple firmly in position.

The invention also provides a "bone staple kit" comprising a range of components which the system may use to construct a custom staple to suit a particular surgical procedure. For example, a bone staple may be constructed by providing first and second staple legs, each having an attached apertured guide member. A first toothed member is provided for slidable insertion within the guide members and second and third toothed members are provided for ratchetable engagement with the first toothed member to hold it in position relative to the first and second staple legs respectively.

DETAILED DESCRIPTION OF THE PREFERRED EMBODIMENT

Basic Tarsal Osteotomy Staple

FIGS. 1 through 6 depict one embodiment of a basic tarsal osteotomy staple generally designated 10. Staple 10 has first and second staple legs 12, 14 which may be driven into the bone segments which are to be joined with the staple. A slidably adjustable ratchet means is provided for coupling first and second legs 12, 14 together and for lockably positioning the legs a selected distance apart from one another. More particularly, the ratchet means comprises a first toothed member 16 affixed to first leg 12 to project at an angle therefrom. As depicted in the drawings, first toothed member 16 projects from first leg 12 at an angle of about 90° in the basic tarsal osteotomy staple, although this angle may, if circumstances require, be varied to accommodate particular surgical techniques. The ratchet means also comprises a barrel-like guide member 18 which is affixed to second leg 14 to project at an angle therefrom. In the basic tarsal osteotomy staple, guide member 18 projects from second leg 14 at an angle of about 90°, although this angle may also vary to accommodate particular surgical techniques. Guide member 18 has a longitudinal aperture 20 through which first toothed member 16 may be slidably advanced to couple guide member 18 with first toothed member 16, thereby positioning first leg 12 relative to second leg 14. Longitudinal aperture 20 and first toothed member 16 are shaped and sized such that first toothed member 16 is snugly, slidably received within longitudinal aperture 20. The ratchet means further comprises a second toothed member 22 which is coupled to guide member 18 (for example, by spot welding the inner surface of downwardly projecting lug 24 to the outer surface of second leg 14) such that member 22 projects along trough 26 provided inside the base of guide member 18 and such that the teeth 28 of member 22 project upwardly into longitudinal aperture 20 for ratchetable engagement with the teeth of first toothed member 16, as member 16 is slidably advanced through guide member 18. Stainless steel is a preferred material for constructing the components which make up staple 10.

Preferably, members 16 and 22 ratchetably engage one another inside the region between first and second legs 12, 14 (as opposed to engagement outside the region between legs 12, 14 as would occur if member 16 were toothed on its upper surface and member 22 were constructed to lie atop member 16). The preferred arrangement facilitates the provision of a smooth, low profile upper surface on members 16 and 18, thus minimizing patient discomfort after the surgical site is closed over the staple. Moreover, the preferred arrangement aforesaid improves the holding capability of the ratchet mechanism, as compared with that of a staple having a ratchet mechanism arranged to engage outside the region between staple legs 12 and 14.

The surface of guide member 18 which covers trough 26 to define longitudinal aperture 20 serves as a "shield means" for preventing fouling of the region in which first toothed member 16 ratchetably engages second toothed member 22. This ensures that staple 10 may be adjusted to attain maximum compressive force at the osteotomy site. Without a comparable shield means the region in which the teeth of member 16 engage those of member 22 could become fouled by tissue or other foreign matter, thus impairing the ability to compress the staple or adversely affecting the holding power of the ratchet mechanism.

A "gripping means" such as a pair of opposed notches 30, 32 or a pair of opposed lugs (not shown) may be provided on staple legs 12, 14 so that staple 10 may be gripped by a suitable pliers type staple manipulating tool for inserting, positioning, compressing, removing or otherwise handling staple 10.

In operation, the staple halves comprising first leg 12 and first toothed member 16 (as one half) and second leg 14, guide member 18 and second toothed member 22 (as the other half) are assembled by slidably advancing first toothed member 16 through longitudinal aperture 20 until teeth 28 of member 22 engage the teeth of member 16. The separation distance between staple legs 12, 14 is then adjusted by moving legs 12, 14 toward one another such that member 16 is further advanced through longitudinal aperture 20. The ratchet mechanism permits such advancement, but prevents movement in the opposite direction. That is, the ratchetable engagement of teeth 28 of member 22 with the teeth of member 16 holds staple legs 12, 14 a selected distance apart from one another and prevents movement of legs 12, 14 away from one another. Once adjusted as aforesaid, staple legs 12, 14 are driven into the opposed ends of the bone segments which are to be joined, until the toothed undersurface of first toothed member 16 and the undersurface of second toothed member 22 lie closely proximate the outer surface of the bone. A suitable pliers type compression tool is then used to grip notches 30 and 32 and apply a compressive force between the ends of staple legs 12, 14 which protrude from the bone, thus urging the ends of the bone segments firmly against one another and ensuring, due to the holding power of the ratchet mechanism, that the bone segments remain compressed together after the compression tool is removed, the surgical site closed and the healing process underway.

The staple of FIGS. 1 through 6 may be strengthened by providing a "reinforcing means" such as a flange (not shown) affixed between the upper inside surface of first leg 12 and the abutting undersurface of first toothed member 16. The reinforcing means strengthens staple 10 by holding first leg 12 in position relative to first toothed member 16 when compressive forces are applied to staple 10 as aforesaid. A corresponding reinforcing flange may be provided between the upper inside surface of second leg 12 and the abutting undersurface of guide member 18.

The staple of FIGS. 1 through 6 may also incorporate "retention means" such as flanges 34 (shown only in FIG. 6) on each of staple legs 12 and 14. Flanges 34 are for retaining the staple legs within bone into which staple 10 is driven.

Metatarsal Osteotomy Staple

Figures 1, 2, 3, 4, 5:
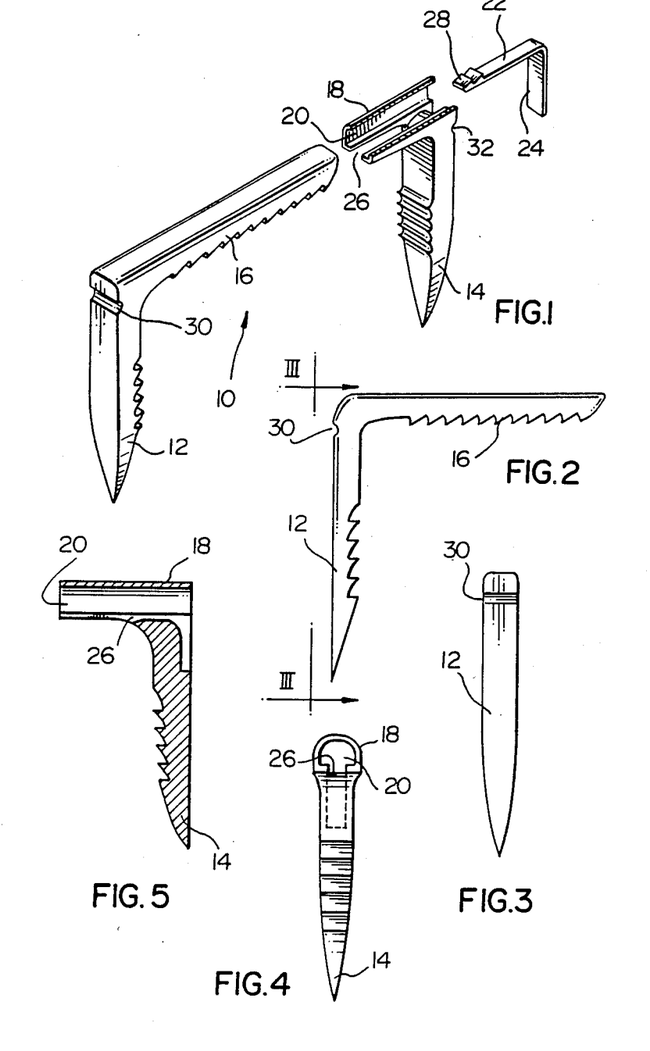
FIG. 1 is a partially fragmented, exploded pictorial illustration of a tarsal osteotomy bone staple in accordance with the invention.
FIG. 2 is an exploded front elevation view of the components which comprise the staple of FIG. 1.
FIG. 3 is a side elevation view taken with respect to line 3≦3 of FIG. 2.
FIG. 4 is a side elevation view taken with respect to line 4—4 of FIG. 2.
FIG. 5 is a cross-sectional front elevation view taken with respect to line 5—5 of FIG. 4.
Figure 6:
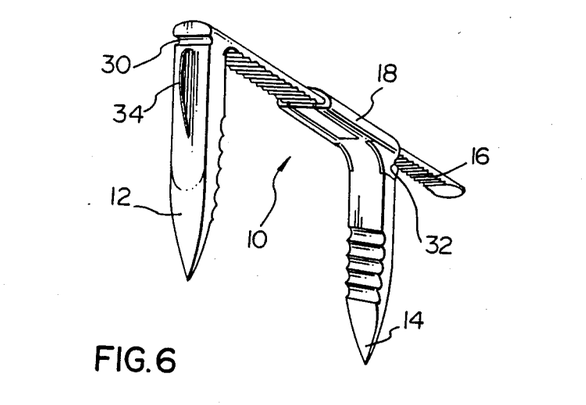
FIG. 6 is a pictorial illustration of an assembled staple comprising the components illustrated in FIGS. 1 through 5.
Figures 7, 8A:
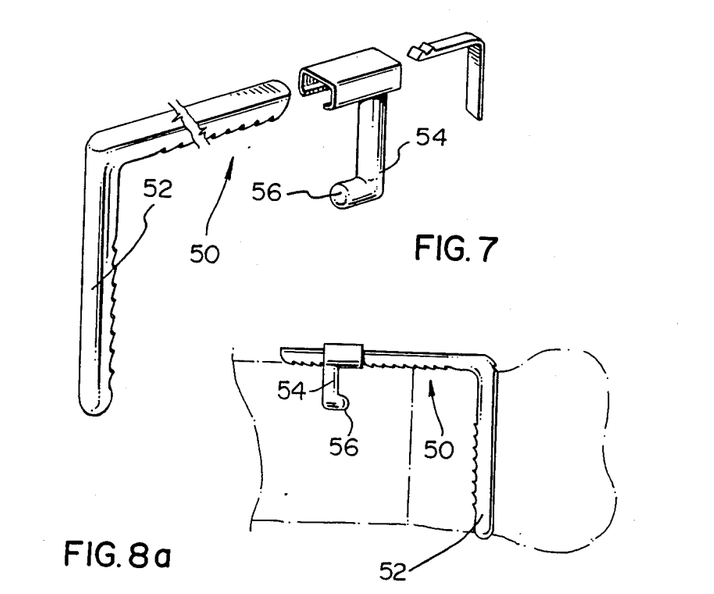
FIG. 7 is an exploded pictorial illustration of a metatarsal osteotomy staple in accordance with the invention.
FIG. 8a is a pictorial illustration showing how the staple of FIG. 7 may be placed at the surgical site.

FIG. 7 depicts a metatarsal osteotomy staple 50 which is structurally similar to basic tarsal osteotomy staple 10. The essential differences include the provision of staple legs 52, 54 of differing lengths, either or both of which may be round in cross-section; and the provision of a hooked projection 56 on the end of leg 54. Staple leg 52 is sized such that it may be passed through the cortex on both sides of a bone (see FIG. 8a), whereas staple leg 54 is shortened such that it passes through the cortex on only one side of the bone. Projection 56 prevents staple leg 54 from slipping out of the bone. The configuration aforesaid allows staple 50 to "toggle" as the osteotomy is closed, ensuring firm closure.

Figure 8B:
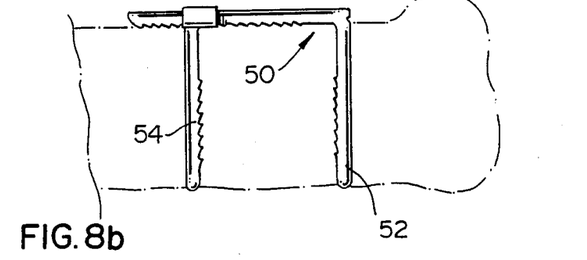
FIG. 8b is a pictorial illustration showing placement of an alternative metatarsal osteotomy staple at the surgical site.

FIG. 8b depicts an alternative metatarsal osteotomy staple which does not incorporate a hooked projection comparable to that of the staple depicted in FIG. 8a, but which does have staple legs which may each pass through the cortex on both sides of the bone, which may be desirable in some cases.

High Tibial Osteotomy Staple

Figure 9:
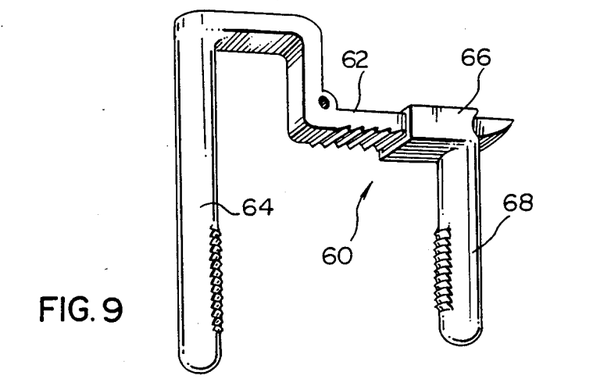
FIG. 9 is a pictorial illustration of a high tibial osteotomy staple in accordance with the invention.

FIG. 9 depicts a high tibial osteotomy staple 60 which is structurally similar to basic tarsal osteotomy staple 10. The essential difference is the provision, in high tibial osteotomy staple 60, of a "stepped" toothed member 62 which is affixed to and projects outwardly from staple leg 64 for ratchetable engagement with cooperating member 66 on staple leg 68. The stepped configuration of member 62 offsets staple leg 64 with respect to staple leg 68, allowing the surgeon to change the relative angle of bone segments which are compressed together with the aid of staple 60.

Figure 10:
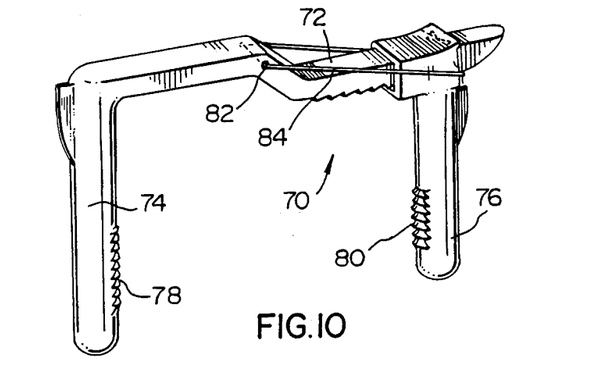
FIG. 10 is a pictorial illustration of an alternative high tibial osteotomy staple in accordance with the invention.
Figures 13A, 13B, 13C:
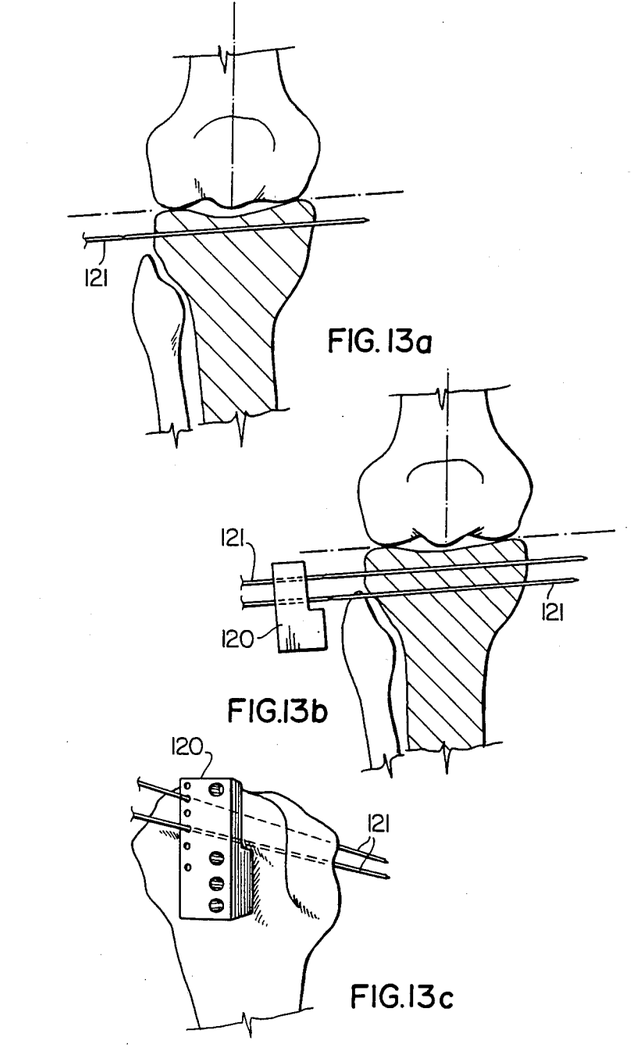
FIGS. 13a through 13i illustrate the sequence of steps in which an osteotomy may be performed with the aid of a staple like that depicted in FIGS. 9 or 10.
Figure 13D:
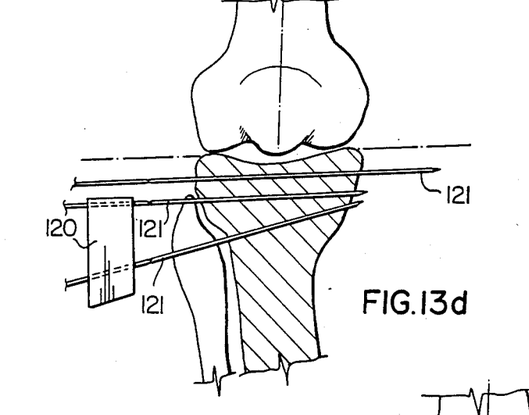
Figures 13E, 13F:
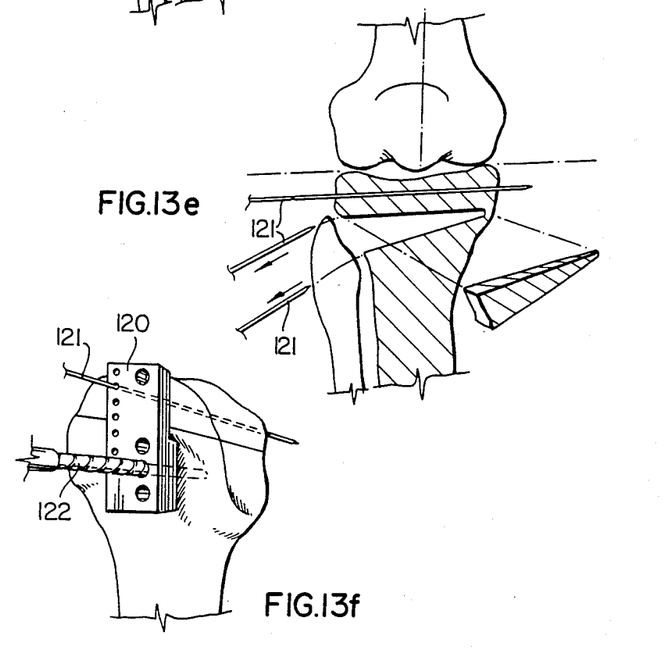
Figures 13G, 13H, 13I:
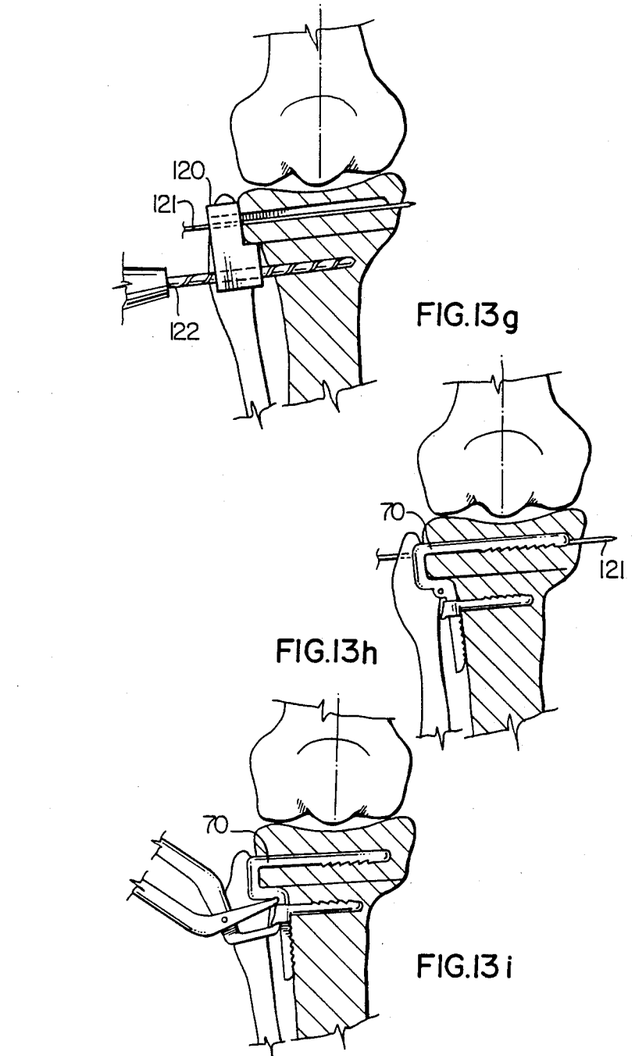

FIG. 10 depicts an alternative high tibial osteotomy staple 70 which is again structurally similar to basic tarsal osteotomy staple 10, but which has a stepped toothed member 72 similar to member 62 of staple 60. The legs 74, 76 of staple 70 are round in cross-section. A jig 120 (see FIGS. 13b, 13c, 13d, 13f and 13g) having apertures corresponding to the diameter of staple legs 74, 76 is positioned over the osteotomy site with the aid of wires 121 and drill 122 (FIGS. 13f and 13g) is then passed through the jig apertures to drill holes in the ends of the opposing bone segments. The separation distance between staple legs 74, 76 is then adjusted as described above with reference to basic tarsal osteotomy staple 10 and staple 70 is then inserted into the drilled holes (FIG. 13h). Serrations 78, 80 on the insides of legs 74, 76 serve as a "staple retention means" to grip the bone when legs 74, 76 are ratchetably compressed toward one another (FIG. 13i), thus ensuring that staple 70 remains firmly seated at the osteotomy site. The tops of staple legs 74, 76 may each be provided with a "retention means", such as sharp, outwardly flared flanges which cut into the cortex as staple 70 is driven into position, further ensuring firm seating of staple 70 at the osteotomy site. An aperture 82 is provided through stepped member 72 as shown in FIG. 10. Once staple 70 has been driven into position and ratchetably compressed to seat it firmly at the osteotomy site a wire 84 may be passed through aperture 82 and the wire ends twisted together beneath that portion of member 72 which projects through staple leg 76, thereby further enhancing the holding power of staple 70.

Knee Fusion Staple

Figure 11:
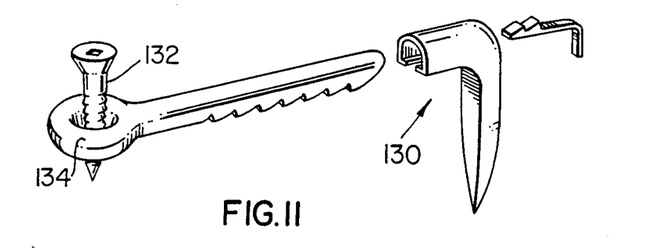
FIG. 11 is a pictorial illustration of one embodiment of a knee fusion staple in accordance with the invention.

FIG. 11 depicts one embodiment of a knee fusion staple 130 which is again structurally similar to basic tarsal osteotomy staple 10; the essential difference being the substitution of screw 132 and eyelet 134 for first leg 12 of staple 10. (A knee fusion staple would also be larger than basic tarsal osteotomy staple 10.) A round or square pin could also be used in place of screw 132 and eyelet 134. These various configurations are well suited to use in knee fusion operations.

Bone Staple Kit

Figure 12:
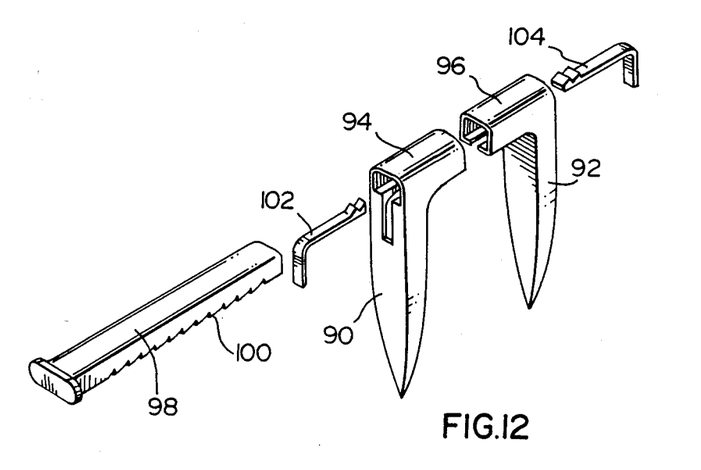
FIG. 12 is a pictorial illustration of a few components which together comprise a portion of a staple kit from which a staple having selected characteristics may be assembled.

FIG. 12 is a pictorial illustration of a range of components from which a staple having selected characteristics may be assembled. More particularly, FIG. 12 illustrates a pair of staple legs 90, 92 which resemble legs 12, 14 of basic tarsal osteotomy staple 10. It will however be understood that a kit of staple components may include alternate staple legs of round, rectangular or other cross-sections; of different lengths; having hooked projections similar to hooked projection 56 of metatarsal osteotomy staple 50, etc. Staple legs 90, 92 are provided with longitudinally apertured guide members 94, 96 respectively which are affixed to and project at right angles from legs 90, 92 respectively. Cross-piece 98 having toothed undersurface 100 is sized for snug, slidable projection through the aligned apertures of guide members 94, 96. Toothed members 102, 104 are slidably insertable into troughs provided inside the bases of guide members 94, 96 respectively such that the teeth of members 102, 104 ratchetably engage the teeth of crosspiece 98 to hold the assembled staple firmly together. Although members 102, 104 are shown separately, they would in practice be spot welded or otherwise attached to the staple legs.

As will be apparent to those skilled in the art in the light of the foregoing disclosure, many alterations and modifications are possible in the practice of this invention without departing from the spirit or scope thereof. For example, the aforementioned bone staple kit may include components having characteristics of any of the staples herein described, thereby facilitating custom construction, by the surgeon, of a strong staple to suit the needs of a particular surgical procedure. Moreover, those skilled in the art will appreciate that the invention need not be restricted to bone staples per se, but may be applied to situations in which bone is to be grasped and/or situations in which objects are to be fastened to bone. Accordingly, the scope of the invention is to be construed in accordance with the substance defined by the following claims.

I claim:

1. A bone staple for compressibly sustaining joinder of first and second bone segments comprising:
    a first downwardly extending elongated staple leg having an upper end and a lower end for securely penetrating said first bone segment;

a second downwardly extending elongated staple leg having an upper end and a lower end for securely penetrating said second bone segment; and ratchet means for adjustably and compressibly coupling said first and second staple legs together and for lockably positioning said staple legs a selected distance apart from one another, said ratchet means comprising a first elongated member having a relatively smooth upper surface and a lower surface, and extending at an angle from the upper end of said first staple leg in a direction toward said second staple leg and fixed to said first staple leg, said first elongated member having a plurality of spaced downwardly extending ratchet teeth on the lower surface of said first elongated member, said ratchet means further comprising a second elongated member having an elongated guide member extending at an angle from the upper end of said second staple leg and fixed thereto, said first elongated member being receivable within said guide member, said guide member having an upper wall, a bottom wall and enclosing side walls forming a guide slot through which said first elongated member extends, said ratchet means further including an elongated ratchet member having an upper surface and a lower surface receivable within said guide slot and fixedly secured within said guide slot, said ratchet member having a plurality of upwardly extending spaced ratchet teeth thereon for ratchably engaging said ratchet teeth on said first elongated member whereby the walls of said guide member encompass the engagement of the ratchet teeth of said ratchet member and said first elongated member to provide a shield to prevent fouling of the area of ratchet engagement.

2. A bone staple as defined in claim 1, wherein said first toothed member projects from said first leg at an angle of about ninety degrees and wherein said guide member projects from said second leg at an angle of about ninety degrees.

3. A bone staple as defined in claim 1, further comprising gripping means on said first and second legs respectively for gripping of said staple by a staple manipulating tool.

4. A bone staple as defined in claim 1, wherein said staple legs each comprise retention means for retaining said legs within bone into which said staple is driven.

5. A bone staple as defined in claim 1, wherein said staple legs are of different lengths.

6. A bone staple as defined in claim 1, wherein said staple legs are round in cross-section.

7. A bone staple as defined in claim 1, further comprising a hooked projection on the end of one of said staple legs.

8. A bone staple as defined in claim 1, further comprising hooked projections on the lower ends of each of said staple legs.

9. A bone staple as defined in claim 1, wherein said first elongated member is stepped.

10. A bone staple as defined in claim 1, further comprising an aperture through said first elongated member and a wire for passage through said aperture and fastening over said second staple leg.

11. A bone staple as defined in claim 1, wherein said ratchet means comprises:
(a) a first apertured guide member affixed to said first staple leg;
(b) a second apertured guide member affixed to said second staple leg;
(c) a first toothed member for slidable insertion within said first and second guide members;
(d) a second toothed member ratchetably engageable with said first toothed member to hold said first toothed member in position relative to said first staple leg; and,
(e) a third toothed member ratchetably engageable with said first toothed member to hold said first toothed member in position relative to said second staple leg.

* * * * *